United States Patent
Hong et al.

(10) Patent No.: US 11,453,643 B2
(45) Date of Patent: Sep. 27, 2022

(54) PREPARATION METHOD FOR POLYTHIOL HAVING IMPROVED STORAGE STABILITY

(71) Applicant: SKC CO., LTD., Gyeonggi-do (KR)

(72) Inventors: Seung Mo Hong, Incheon (KR); Hyeon Myeong Seo, Ulsan (KR); Junghwan Shin, Gyeonggi-do (KR); Jeongmoo Kim, Gyeonggi-do (KR)

(73) Assignee: SKC CO., LTD., Gyeonggi-do (KR)

( * ) Notice: Subject to any disclaimer, the term of this patent is extended or adjusted under 35 U.S.C. 154(b) by 0 days.

(21) Appl. No.: 17/048,743

(22) PCT Filed: Apr. 25, 2019

(86) PCT No.: PCT/KR2019/005007
§ 371 (c)(1),
(2) Date: Oct. 19, 2020

(87) PCT Pub. No.: WO2019/209046
PCT Pub. Date: Oct. 31, 2019

(65) Prior Publication Data
US 2021/0171491 A1  Jun. 10, 2021

(30) Foreign Application Priority Data
Apr. 25, 2018  (KR) .......... 10-2018-0048043

(51) Int. Cl.
| | |
|---|---|
| C07C 319/28 | (2006.01) |
| C07C 319/08 | (2006.01) |
| C07C 319/20 | (2006.01) |
| C07D 339/08 | (2006.01) |
| C07C 321/04 | (2006.01) |

(52) U.S. Cl.
CPC .......... *C07C 319/28* (2013.01); *C07C 319/08* (2013.01); *C07C 319/20* (2013.01); *C07D 339/08* (2013.01); *C07C 321/04* (2013.01)

(58) Field of Classification Search
CPC .... C07C 319/28; C07C 319/20; C07D 339/08
See application file for complete search history.

(56) References Cited

U.S. PATENT DOCUMENTS

| | | | | |
|---|---|---|---|---|
| 5,326,501 A | * | 7/1994 | Ohkubo | G02B 1/04 252/582 |
| 5,608,115 A | * | 3/1997 | Okazaki | C08G 18/52 568/61 |
| 2015/0133692 A1 | * | 5/2015 | Kawaguchi | C08G 18/3876 568/57 |
| 2019/0062270 A1 | | 2/2019 | Kageyama et al. | |

FOREIGN PATENT DOCUMENTS

| | | |
|---|---|---|
| JP | 06-025223 A | 2/1994 |
| JP | 4217018 B2 | 1/2009 |
| KR | 10-0180926 B1 | 5/1999 |
| KR | 10-1455645 B1 | 10/2014 |
| KR | 10-2014-0141723 A | 12/2014 |
| KR | 10-2017-0078139 A | 7/2017 |
| KR | 10-2018-0024513 A | 3/2018 |
| WO | 2018/003059 A1 | 1/2018 |

OTHER PUBLICATIONS

Extended European Search Report issued by the European Patent Office dated Mar. 4, 2022.

* cited by examiner

*Primary Examiner* — Rosalynd A Keys
(74) *Attorney, Agent, or Firm* — IP & T Group LLP (57) ABSTRACT

According to one embodiment, in producing polythiols in a manner similar to a conventional method, a polythiol having improved storage stability may be produced in a convenient manner by adjusting reaction conditions so as to prevent thiourea from remaining within products. In particular, the equivalent weight of thiourea to be used in a reaction may be adjusted to a predetermined range, thereby reducing the amount of unreacted thiourea, and thiourea may be removed once more in a sub sequent process, thereby effectively removing remaining thiourea while achieving a high yield. The polythiol thus produced does not contain residual thiourea, and thus does not show discoloration or cloudiness caused by precipitates even under prolonged storage or high-temperature conditions.

6 Claims, 1 Drawing Sheet

PREPARATION METHOD FOR POLYTHIOL HAVING IMPROVED STORAGE STABILITY

This application is a national stage application of PCT/KR2019/005007 filed on Apr. 25, 2019, which claims priorities of Korean patent application number 10-2018-0048043 filed on Apr. 25, 2018. The disclosure of each of the foregoing applications is incorporated herein by reference in its entirety.

TECHNICAL FIELD

Embodiments relate to a process for preparing a polythiol having improved storage stability. More specifically, the embodiments relate to a process for preparing a polythiol having improved storage stability by restricting the conditions in the process of reacting an organohalide or a polyol containing a sulfur atom with thiourea and hydrolyzing the resultant. In addition, the embodiments relate to a polythiol prepared by the above process and having improved storage stability.

BACKGROUND ART

Since plastics optical materials are lightweight, hardly breakable, and excellent in dyeability as compared with optical materials made of inorganic materials such as glass, they are widely used as optical materials for eyeglass lenses, camera lenses, and the like. In recent years, there has been a demand for optical materials having higher performance in terms of high transparency, high refractive index, low specific gravity, high thermal resistance, and high impact resistance.

Polythiourethane among plastic optical materials is widely used as an optical material by virtue of its excellent optical characteristics and excellent mechanical properties. Polythiourethane may be prepared by reacting a polythiol and an isocyanate. Lenses made from polythiourethane are widely used by virtue of their high refractive index, lightweight, and relatively high impact resistance.

Polythiols, one of the main raw materials of polythiourethane, are produced by reacting an organohalide or a polyol containing a sulfur atom with thiourea to produce an isothiouronium salt and hydrolyzing it in the presence of a basic aqueous solution (see Korean Patent No. 180926). Meanwhile, the polythiols produced through this process contain a trace amount of impurities, which affects the quality of the final optical materials. Thus, efforts have been made to improve the quality of polythiols and final optical materials by using high-purity raw materials.

DETAILED DESCRIPTION OF THE INVENTION

Technical Problem

Despite the efforts to improve the quality of polythiols and final optical materials by using high-purity raw materials in the conventional technologies, there has been a problem that discoloration or cloudiness due to precipitates takes place when the polythiols thus prepared are stored for a long period of time or under high-temperature conditions. As a result of research conducted by the present inventors, it has been discovered that thiourea remaining in the polythiols prepared by the conventional technologies has a profound impact on the storage stability of the polythiols.

In the conventional process for preparing a polythiol in which an organohalide or a polyol containing a sulfur atom is reacted with thiourea, an excess of thiourea is generally used relative to the reaction equivalent in order to increase the yield of the polythiol. Thus, unreacted thiourea remains in the reaction product, resulting in discoloration and cloudiness when the product is stored for a long period of time or under high-temperature conditions, which has a fatal impact on the optical properties of the final optical lenses.

Accordingly, the embodiments aim to provide a process for preparing a polythiol without residual thiourea. In addition, the embodiments aim to provide a polythiol prepared by the above process and having enhanced storage stability.

Solution to the Problem

According to an embodiment, there is provided a process for preparing a polythiol, which comprises reacting 1 equivalent of an organohalide or a polyol containing a sulfur atom with 111 to 1.30 equivalents of thiourea; hydrolyzing the reaction product to obtain a crude polythiol; and subjecting the crude polythiol to acid washing and water washing to remove unreacted thiourea.

According to another embodiment, there is provided a polythiol, which has an L* value of 95 or more in the CIE L*a*b* color coordinate upon storage at a temperature of 130° C. for 8 hours, wherein the change (ΔL*) in the L* value according to the following Equation (I) is 5 or less:

$$\Delta L^* = L^*_{initial} - L^*_{final} \quad (I)$$

In the above equation, $L^*_{initial}$ is the L* value before storage under the above conditions, and $L^*_{final}$ is the L* value upon storage under the above conditions.

Advantageous Effects of the Invention

According to the embodiments, although a polythiol is prepared in a similar manner to that of the prior art, the polythiol can have improved storage stability by adjusting the reaction conditions such that there remains no thiourea in the reaction product.

Specifically, the equivalent amount of thiourea used in the reaction is adjusted to a specific range to reduce the amount of unreacted thiourea, and thiourea is removed again in the subsequent process, whereby it is possible to achieve a high yield while residual thiourea is effectively removed.

The polythiol thus prepared does not contain residual thiourea, so that discoloration or cloudiness due to precipitates does not take place even when it is stored for a long period of time or under high-temperature conditions.

Therefore, even if the polythiol prepared according to the above embodiment is stored for a long period of time or subjected to a high-temperature process, it can produce a polythiourethane having excellent optical properties. Thus, it can be advantageously used for an optical material such as eyeglass lenses, camera lenses, and the like.

BEST MODE FOR CARRYING OUT THE INVENTION

Hereinafter, the embodiments will be described in detail.

The process for preparing a polythiol according to an embodiment comprises reacting 1 equivalent of an organohalide or a polyol containing a sulfur atom with 1.11 to 1.30 equivalents of thiourea; hydrolyzing the reaction product to obtain a crude polythiol; and subjecting the crude polythiol to acid washing and water washing to remove unreacted thiourea.

Hereinafter, each step will be described in detail.

First, an organohalide or a polyol containing a sulfur atom is prepared.

The organohalide or polyol containing a sulfur atom can be prepared in a manner well known in the art.

For example, diallyl disulfide of the following Formula 1 is reacted with sulfuryl chloride, bromine gas, or chlorine gas to prepare an organohalide represented by the following Formula 2.

[Formula 1]

[Formula 2]

In Formula 2, X is halogen, for example, Cl or Br.

In addition, an epihalohydrin of the following Formula 4 is reacted with 2-mercaptoethanol of the following Formula 5 to prepare a compound of the following Formula 5a.

[Formula 4]

[Formula 5]

[Formula 5a]

In Formulae 4 and 5a, X is halogen, for example, Cl, Br, or I.

Here, 0.9 to 1.1 moles of the compound of Formula 4 may be used per 1 mole of the compound of Formula 5.

Triphenylphosphine or a basic catalyst may be used as a reaction catalyst. Examples of the basic catalyst may include tertiary amines such as trimethylamine, triethylamine, tributylamine, and pyridine; tertiary ammonium salts such as trimethylammonium chloride, trimethylammonium bromide, triethylammonium chloride, triethylammonium bromide, tributylammonium chloride, and tributylammonium bromide; and metallic bases such as sodium hydroxide, potassium hydroxide, and sodium carbonate. The amount of the reaction catalyst used may be 0.01 part by weight to 3 parts by weight, or 0.1 part by weight to 1 part by weight, based on 100 parts by weight of the total amount of the compounds of Formulae 4 and 5.

Water or alcohols may be used as a reaction solvent. Examples of the alcohol include methanol, ethanol, propanol, and butanol, which is not limited as long as it is a solvent that can be mixed with the basic catalyst.

The reaction temperature may be 10° C. to 40° C., or 15° C. to 30° C., which can increase the reactivity while side reactions are suppressed.

Thereafter, the compound of the above Formula 5a is further reacted with the compound of the above Formula 5 to prepare a compound of the following Formula 6.

[Formula 6]

Here, 1 to 1.2 moles of the compound of Formula 5 may be used per 1 mole of the compound of Formula 5a.

In addition, the reaction may be carried out in the presence of a metallic base. In such event, the amount of the metallic base used may be 1 mole to 1.2 moles based on 1 mole of the compound of the above Formula 5a. Examples of the metallic base include sodium hydroxide, potassium hydroxide, sodium carbonate, calcium hydroxide, and the like. It is preferable to use sodium hydroxide or potassium hydroxide from the viewpoint of cost and reaction efficiency.

Alternatively, an excess of the compound of the above Formula 5 may be added to the compound of the above Formula 4 to directly prepare the compound of the above Formula 6. For example, 1.9 to 2.1 moles of the compound of Formula 5 may be used per 1 mole of the compound of Formula 4.

A metallic base may be used as a reaction catalyst, and water or alcohols may be used as a reaction solvent. The amount of the reaction catalyst used may be 0.9 mole to 1.2 moles based on 1 mole of the compound of the above Formula 4. In addition, the amount of the reaction solvent used may be 10 parts by weight to 300 parts by weight based on 100 parts by weight of the total amount of the compounds of Formulae 3 and 4.

In addition, the compound of the above Formula 5a may be reacted with sodium sulfide to prepare a compound of the following Formula 7.

[Formula 7]

Sodium sulfide is usually present as a hydrate. Sodium sulfide pentahydrate or sodium sulfide hydrate may be commercially available for use.

Sodium sulfide may be diluted in water to 10% by weight to 50% by weight, which may be slowly introduced for the reaction. The reaction temperature may be 10° C. to 30° C. or 15° C. to 25° C.

The organohalide or polyol containing a sulfur atom thus prepared may be separated or purified to be used in the next step or may be used in the next step as the resultant without separate separation or purification.

Thereafter, the organohalide or polyol containing a sulfur atom may be reacted with thiourea.

According to an embodiment, 1.11 to 1.30 equivalents of thiourea is used in the reaction based on 1 equivalent of the organohalide or polyol. For example, the equivalent range of thiourea may be 1.11 to 1.25, 1.15 to 1.25, 1.20 to 1.25, 1.11 to 1.20, 1.11 to 1.15, or 1.15 to 1.20. If thiourea is used at an equivalent within the above range, the yield may be high while thiourea is hardly contained in the final polythiol.

Specifically, if thiourea is used at an equivalent higher than the above range (for example, 1.4 equivalents) in the reaction, the amount of thiourea remaining in the final polythiol becomes large, making it difficult to be completely removed even by such purification step as washing. As a result, the storage stability of the polythiol may be deteriorated.

In addition, if thiourea is used at an equivalent lower than the above range (for example, 1.1 equivalents) in the reaction, the ratio at which the halogen group of the organohalide or the hydroxyl group of the polyol is substituted with a thiol group decreases, thereby lowering the yield of the polythiol.

According to an example, the polyol may be a polyol having a thioether group, and the polythiol may have a thioether group.

According to a specific example, the organohalide may be a compound of the following Formula 2, and the polythiol may be a compound of the following Formula 3.

[Formula 2]

[Formula 3]

In Formula 2, X is halogen, for example, Cl or Br.

According to another specific example, the polyol may be a compound of the following Formula 7, and the polythiol may be a compound of the following Formula 8a.

[Formula 7]

[Formula 8a]

Alternatively, the polyol may be a compound of the following Formula 7, and the polythiol may be a mixture of compounds of the following Formula 8a to 8c.

[Formula 7]

[Formula 8a]

[Formula 8b]

[Formula 8c]

According to still another specific example, the polyol may be a compound of the following Formula 6, and the polythiol may be a compound of the following Formula 9.

[Formula 6]

[Formula 9]

The reaction with thiourea may be carried out under reflux conditions.

The reflux temperature may be 60° C. to 130° C., more preferably 90° C. to 120° C. In addition, the reflux time may be 1 hour to 24 hours, more specifically 6 hours to 12 hours.

An isothiouronium salt is produced through the reaction with thiourea as described above.

The isothiouronium salt produced by the reaction with thiourea is subjected to hydrolysis. Specifically, upon the reaction with thiourea, hydrolysis is carried out under basic conditions. Such a basic compound as sodium hydroxide, potassium hydroxide, sodium carbonate, ammonia, or the like may be used for the basic conditions.

The basic compound may be employed in an amount of 1.0 to 2.5 equivalents, more specifically 1.3 to 1.8 equivalents, based on 1 equivalent of the isothiouronium salt. For example, the basic compound may be employed in the form of an aqueous solution.

An organic solvent may be added before the basic compound is employed. The amount of the organic solvent added may be 0.1 to 3.0 times in volume, more specifically 0.2 to 2.0 times in volume, the amount of the isothiouronium salt solution. Examples of the organic solvent include toluene, xylene, chlorobenzene, dichlorobenzene, and the like. Toluene is preferred for the effect of suppressing the generation of by-products.

The hydrolysis temperature may be 10° C. to 130° C., more specifically 30° C. to 80° C. The hydrolysis time may be 0.1 hour to 6 hours, more specifically 0.5 hour to 4 hours.

Crude polythiol may be obtained through such hydrolysis.

The crude polythiol may be subjected to subsequent steps such as washing, purification, dewatering, and the like.

According to an embodiment, the polythiol obtained upon the hydrolysis is subjected to acid washing and water washing to remove unreacted thiourea.

Specifically, the acid washing and water washing may be repeatedly carried out until no thiourea is detected in the waste liquid. For example, the acid washing and water washing may be carried out twice or more, respectively.

According to a specific example, acid washing of the polythiol obtained upon the hydrolysis is first repeated to remove unreacted thiourea until no thiourea is detected in the waste liquid. The acid for the acid washing may be an inorganic acid and is preferably in the form of an aqueous solution.

An aqueous acid solution such as an aqueous sulfuric acid solution or an aqueous hydrochloric acid solution may be used for the acid washing. More specifically, the acid washing may be carried out using an aqueous acid solution containing 1% by weight to 40% by weight (or 1% by weight to 20% by weight) of an inorganic acid selected from the group consisting of hydrochloric acid, nitric acid, sulfuric acid, phosphoric acid, boric acid, carbonic acid, hydrofluoric acid, and bromic acid. The acid washing may be carried out while the concentration of the aqueous acid solution is lowered as the acid washing is repeated.

Thereafter, water washing is carried out to adjust the pH of the polythiol.

It is advantageous for securing the quality of polythiol to repeatedly carry out the water washing until the waste liquid becomes neutral, for example, having a pH of 6 to 7.

Thiourea remaining in the polythiol may be completely removed through the acid washing and water washing.

In particular, according to the above embodiment, since the equivalent of thiourea has been adjusted to a specific range to be used in the reaction in the previous step, the residual thiourea can be readily removed through the acid washing and water washing.

Thus, according to the process of an embodiment, it is possible to produce a polythiol in high yield while the residual thiourea is effectively removed.

According to another embodiment, there is provided polythiol prepared by the above process.

Discoloration or cloudiness due to precipitates does not take place even when the polythiol is stored for a long period of time or under high-temperature conditions.

That is, the polythiol has an L* value of 95 or more in the CIE L*a*b* color coordinate upon storage at a temperature of 130° C. for 8 hours, and the change (ΔL*) in the L* value according to the following Equation (I) is 5 or less:

$$\Delta L^* = L^*_{initial} - L^*_{final} \qquad (I)$$

in the above Equation, $L^*_{initial}$ is the L* value before storage under the above conditions, and $L^*_{final}$ is the L* value upon storage under the above conditions.

Specifically, the L* value in the CIE L*a*b* color coordinate of the polythiol upon storage at a temperature of 130° C. for 8 hours may be 96 or more, 97 or more, or 98 or more, and the change (ΔL*) in the L* value may be 4 or less or 3 or less.

In addition, the change (ΔL*) in the L* value of the polythiol upon storage at a temperature of 60° C. for 7 days may be 3 or less or 2 or less.

In addition, the change (ΔL*) in the L* value of the polythiol upon storage at a temperature of 10° C. to 20° C. for 365 days may be 3 or less or 2 or less.

The L* value is an indicator that represents brightness. If the value is 100, the upper limit, it can be viewed as a completely transparent liquid. It can be calibrated with reference to distilled water or ion-exchanged water when the color coordinate is measured. In addition, ΔL* according to the above Formula (I) is related to a change in transparency of a polythiol. As the value is smaller, the transparency is well maintained.

Thus, the polythiol is not deteriorated in quality even when stored under high-temperature conditions or for a long period of time of 1 year or longer.

In addition, the polythiol according to the above embodiment hardly changes in the color value of APHA (American Public Health Association) when stored under high-temperature conditions. Specifically, the change in the color value of APHA may be in the range of 0 to 15, or in the range of 0 to 10, when the polythiol is stored at 80° C. for 30 days.

Since the polythiol is prepared by the process as described above, no thiourea, or a very minute amount of thiourea, is present in the impurities contained therein. For example, the content of thiourea in the polythiol according to the above embodiment may be 100 ppm or less, or 50 ppm or less.

The polythiol may be a bi- or higher-functional, tri- or higher-functional, or tetra- or higher-functional polythiol. For example, the polythiol may be a polythiol having 2 to 10, 2 to 8, 2 to 6, or 2 to 4 thiol groups in the molecule. In addition, the polythiol may have 1 or more of a thioether group (—S—) in the molecule.

For example, the polythiol may be a cyclic polythiol as represented by the above Formula 3. Alternatively, the polythiol may be a linear polythiol as represented by the above Formulae 8a, 8b, 8c, and 9.

Specifically, the polythiol may be a linear aliphatic tri- or higher-functional polythiol. Examples thereof include 1,2,3-propanetrithiol, tetrakis(mercaptomethyl)methane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 1,1,3,3-tetrakis(mercaptomethylthio)propane,1,1,2,2-tetrakis(mercaptomethylthio)ethane, 4,6-bis(mercaptomethylthio)-1,3-dithiacyclohexane, tris(mercaptomethylthio)methane, and tris(mercaptoethylthio)methane.

In addition, the polythiol according to the above embodiment may have a purity of 90% by weight or more, 95% by weight or more, 97% by weight or more, 99% by weight or more, or 99.5% by weight or more.

According to an embodiment, there is provided a polymerizable composition, which comprises the polythiol and an isocyanate.

The polymerizable composition may comprise a polythiol and an isocyanate in a mixed state or in a separated state. That is, the polythiol and the isocyanate in the polymerizable composition may be in a state of being compounded in contact with each other or separated from each other so as not to contact each other.

The polymerizable composition may comprise the polythiol according to the above embodiment in an amount of 100% by weight.

In addition, if necessary, the polymerizable composition may further comprise a polythiol different from the polythiol according to the above embodiment in addition thereto.

In such event, the polymerizable composition may comprise the polythiol according to the above embodiment in an amount of 5 parts by weight to 70 parts by weight based on 100 parts by weight of the entire polythiols.

The different polythiol may be an aromatic polythiol. Examples thereof include methanedithiol, 1,2-ethanedithiol, pentaerythritol tetrakis(2-mercaptoacetate), pentaerythritol tetrakis(3-mercaptopropionate), bis(mercaptoethyl) sulfide, 2,5-dimercaptomethyl-1,4-dithiane, 2,5-dimercaptomethyl-1,4-dithiane, 2,5-dimercapto-1,4-dithiane, 2,5-dimercaptomethyl-2,5-dimethyl-1,4-dithiane and 4,6-bis(mercaptomethylthio)-1,3-dithiane.

The isocyanate may be a conventional one commonly used for the synthesis of polythiourethane.

Specifically, the isocyanate may be selected from the group consisting of aliphatic isocyanate compounds comprising isophorone diisocyanate, dicyclohexylmethane-4,4-diisocyanate, hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl) carbonate, bis(isocyanatoethyl) ether, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyldimethylmethane isocyanate, 2,2-dimethyldicyclohexylmethane isocyanate, bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatopropyl) disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane, 2,5-diisocyanatothiophene, 2,5-bis (isocyanatomethyl) thiophene, 2,5-diisocyanatotetrahydrothiophene, 2,5-bis (isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane; bis(isocyanatoethyl)benzene, bis(isocyanatopropyl)benzene, bis(isocyanatobutyl)benzene, bis(isocyanatomethyl)naphthalene, bis(isocyanatomethyl) diphenyl ether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluene diisocyanate, toluidine diisocyanate, 4,4-diphenylmethane diisocyanate, 3,3-dimethyldiphenylmethane-4,4-diisocyanate, bibenzyl-4,4-diisocyanate, bis (isocyanatophenyl)ethylene, 3,3-dimethoxybiphenyl-4,4-diisocyanate, hexahydrobenzene diisocyanate, hexahydrodiphenylmethane-4,4-diisocyanate, o-xylene diisocyanate, m-xylene diisocyanate, p-xylene diisocyanate, 1,3-bis(isocyanatomethyl)cyclohexane, diphenyl sulfide-2,4-diisocyanate, diphenyl sulfide-4,4-diisocyanate, 3,3-dimethoxy-4,4-diisocyanatodibenzylthioether, bis(4-isocyanatomethylbenzene) sulfide, 4,4-methoxybenzenethioethylene glycol-3,3-diisocyanate, diphenyl disulfide-4,4-diisocyanate, 2,2-dimethyl diphenyl disulfide-5,5-diisocyanate, 3,3-dimethyl diphenyl disulfide-5,5-diisocyanate, 3,3-dimethyl diphenyl disulfide-6,6-diisocyanate, 4,4-dimethyl diphenyl disulfide-5,5-diisocyanate, 3,3-dimethoxydiphenyl disulfide-4,4-diisocyanate, 4,4-dimethoxydiphenyl disulfide-3,3-diisocyanate, and a mixture thereof.

More specifically, 1,3-bis(isocyanatomethyl)cyclohexane, hexamethylene diisocyanate, isophorone diisocyanate, o-xylene diisocyanate, m-xylene diisocyanate, p-xylene diisocyanate, toluene diisocyanate, or the like may be used as the isocyanate.

In addition, the polymerizable composition may further comprise such additives as an internal mold release agent, an ultraviolet absorber, a polymerization initiator, a heat stabilizer, a blueing agent, a chain extender, a crosslinking agent, a light stabilizer, an antioxidant, and a filler, depending on the purpose thereof.

The internal release agent may include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearylammonium salt, dimethylethylcetylammonium salt, triethyldodecylammonium salt, trioctylmethylammonium salt, and diethylcyclohexadodecylammonium salt; and an acidic phosphate ester. It may be used alone or in combination of two or more.

As the ultraviolet absorber, benzophenone-based, benzotriazole-based, salicylate-based, cyanoacrylate-based, oxanilide-based, or the like may be used.

As the polymerization initiator, an amine type, a phosphorus type, an organotin type, an organic copper type, an organic gallium type, an organic zirconium type, an organic iron type, an organic zinc, an organic aluminum, or the like may be used.

As the heat stabilizer, a metal fatty acid salt, a phosphorus compound, a lead compound, or an organotin compound may be used alone or in combination of two or more.

According to still another embodiment, there is provided a polythiourethane-based compound prepared from the polymerizable composition as described above. The polythiourethane-based compound is prepared by polymerizing (and curing) the polythiol composition and the isocyanate compound. The reaction molar ratio of SH groups to NCO groups in the polymerization reaction may be 0.5 to 3.0, particularly 0.6 to 2.0, more particularly 0.8 to 1.3. Within this range, the properties required for an optical material such as refractive index and heat resistance and the balance between them may be improved. Further, the above-mentioned reaction catalyst, which is conventionally used in the production of polythiourethane, may be employed in order to control the reaction rate.

According to still another embodiment, there are provided a molded article produced by curing the polymerizable composition and an optical material consisting of the molded article. The optical material may be produced by polymerizing and molding the polymerizable composition.

First, the polymerizable composition is degassed under a reduced pressure and then injected into a mold for molding an optical material. Such degassing and mold injection may be carried out in a temperature range of, for example, 20° C. to 40° C. Once the composition has been injected into the mold, polymerization is usually carried out by gradually heating the composition from a low temperature to a high temperature.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

Then, the polythiourethane-based optical material is released from the mold.

The optical material may have various shapes by changing the mold used in the production thereof. Specifically, it may be in the form of an eyeglass lens, a camera lens, a light emitting diode (LED), or the like.

The optical material may have a refractive index of 1.65 to 1.75 or 1.65 to 1.70.

The optical material may be an optical lens, specifically a plastic optical lens. If required, the optical lens may be subjected to physical or chemical treatment such as surface polishing, antistatic treatment, hard coat treatment, anti-reflection coat treatment, dyeing treatment, and dimming treatment for the purpose of imparting thereto anti-reflection, hardness, abrasion resistance, chemical resistance, anti-fogging, or fashionity.

MODE FOR CARRYING OUT THE INVENTION

Hereinafter, the embodiments will be described in detail with reference to examples. The following Examples are intended to further illustrate the present invention without limiting its scope.

Example 1: Preparation of a Polythiol

Step (1): Synthesis of a Polyol

A 2-liter, 4-neck reaction flask equipped with a stirrer, a reflux cooling tube, a nitrogen gas purge tube, and a thermometer was charged with 89.1 g (1.14 moles) of 2-mercaptoethanol, 44.8 g of water, and 0.4 g of an aqueous solution of 47% sodium hydroxide. 107.3 g (1.16 moles) of epichlorohydrin was added dropwise to the reaction flask at 10° C. over 4 hours, followed by aging for 1 hour. Thereafter, 261.6 g (0.58 mole) of an aqueous solution of 16.9% sodium sulfide was added dropwise at 25° C. over 1 hour, followed by aging for 3 hours at the same temperature to obtain a polyol.

Step (2): Thiourea Reaction and Hydrolysis

Thereafter, 199.4 g (2.62 moles, about 1.15 equivalents per 1 equivalent of the polyol) of thiourea having a calcium content of 0.05% and a purity of 99.90% obtained by recrystallization in advance was added, followed by aging for 3 hours under the reflux condition at 110° C. After the reaction solution was cooled to 60° C., 360.0 g of toluene and 347.4 g (5.10 mole) of an aqueous solution of 25% ammonia were added to carry out hydrolysis.

Step (3): Removal of Thiourea

The organic layer was separated and washed with 180 g of an aqueous solution of 36% hydrochloric acid. Further, it was washed twice with 180 g of an aqueous solution of 5% hydrochloric acid. It was confirmed by HPLC that there was no thiourea in the waste liquid. The solution washed with acid as described above was subjected to water washing, which was repeated until the pH of the waste liquid became 6 to 7. Thereafter, the polythiol solution was concentrated under a reduced pressure to remove toluene and filtered through a 0.2-μm PTFE filter to obtain 191.4 g of a mixture of polythiols of the above Formulae 8a to 8c.

Example 2: Preparation of a Polythiol

Step (1): Synthesis of a Polyol 88.7 g (1.14 moles) of 2-mercaptoethanol was added dropwise to 50.4 g (0.567 mole) of an aqueous solution of 45% sodium hydroxide to obtain a homogeneous solution. Then, 50.5 g (0.546 mole) of epichlorohydrin was added dropwise thereto over 1.5 hours, followed by stirring with heating for 0.5 hour at 112° C.

Step (2): Thiourea Reaction and Hydrolysis

After it was cooled to room temperature, 270 g (2.66 moles) of an aqueous solution of 36% hydrochloric acid and 143.1 g (1.88 moles, about 1.15 equivalents per 1 equivalent of the polyol) of thiourea were added, followed by stirring for 1.5 hours at 112° C.

Thereafter, 288 g (3.24 moles) of an aqueous solution of 45% sodium hydroxide was added dropwise over 0.5 hour while the temperature was maintained at 20 to 25° C., followed by stirring with heating for 1.5 hours at 110° C.

Step (3): Removal of Thiourea

The organic layer was separated and washed twice with 150 g of an aqueous solution of 5% hydrochloric acid. It was confirmed by HPLC that there was no thiourea in the waste liquid. The solution washed with acid as described above was subjected to water washing, which was repeated until the pH of the waste liquid became 6 to 7. Thereafter, the polythiol solution was concentrated under a reduced pressure to remove toluene and filtered through a 0.2-μm PTFE filter to obtain 138.3 g of the polythiol of the above Formula 9.

Example 3: Preparation of a Polythiol

The procedures of Example 1 were repeated, except that, in Step (2), the amount of thiourea was 215.1 g (2.83 moles, about 1.24 equivalents per 1 equivalent of the polyol). In addition, in Step (3), it washed with an aqueous solution of 36% hydrochloric acid, followed by washing with an aqueous solution of 5% hydrochloric acid three times. It was confirmed by HPLC that there was no thiourea in the waste liquid. Thereafter, the same water washing, concentration under a reduced pressure, and filtration were carried out to obtain 192.7 g of a mixture of the polythiols of the above Formulae 8a to 8c.

Example 4: Preparation of a Polythiol

The procedures of Example 2 were repeated, except that, in Step (2), the amount of thiourea was 144.4 g (1.90 moles, about 1.11 equivalents per 1 equivalent of the polyol). In addition, in Step (3), it washed with an aqueous solution of 36% hydrochloric acid, followed by washing with an aqueous solution of 5% hydrochloric acid once. It was confirmed by HPLC that there was no thiourea in the waste liquid. Thereafter, the same water washing, concentration under a reduced pressure, and filtration were carried out to obtain 134.7 g of the polythiol of the above Formula 9.

Example 5: Preparation of a Polythiol

The procedures of Example 2 were repeated, except that, in Step (2), the amount of thiourea was 169.2 g (2.22 moles, about 1.30 equivalents per 1 equivalent of the polyol). In addition, in Step (3), it washed with an aqueous solution of 36% hydrochloric acid, followed by washing with an aqueous solution of 5% hydrochloric acid four times. It was confirmed by HPLC that there was no thiourea in the waste liquid. The solution washed with acid as described above was subjected to water washing, which was repeated until the pH of the waste liquid became 6 to 7. Thereafter, the same water washing, concentration under a reduced pressure, and filtration were carried out to obtain 130.6 g of the polythiol of the above Formula 9.

Comparative Example 1: Preparation of a Polythiol

The procedures of Example 1 were repeated, except that, in Step (2), the amount of thiourea was 242.9 g (3.19 moles, about 1.40 equivalents per 1 equivalent of the polyol). In addition, in Step (3), it washed with an aqueous solution of 36% hydrochloric acid, followed by washing with an aqueous solution of 5% hydrochloric acid five times. But thiourea was detected in the waste liquid. The reaction solution washed with acid as described above was subjected to water washing, which was repeated until the pH of the waste liquid became 6 to 7. But thiourea was detected in the waste liquid. Thereafter, the same water washing, concentration under a reduced pressure, and filtration were carried out to obtain 171.7 g of a mixture of the polythiols of the above Formulae 8a to 8c.

Comparative Example 2: Preparation of a Polythiol

The procedures of Example 2 were repeated, except that, in Step (3), it washed with an aqueous solution of 36% hydrochloric acid without further acid washing. Water washing was repeated until the pH of the waste liquid became 6 to 7. Thiourea that had not been removed was detected in the waste liquid. Thereafter, the same concentration under a reduced pressure and filtration were carried out to obtain 140.7 g of the polythiol of the above Formula 9.

Comparative Example 3: Preparation of a Polythiol

The procedures of Example 1 were repeated, except that, in Step (2), the amount of thiourea was 182.2 g (2.39 moles, about 1.05 equivalents per 1 equivalent of the polyol) to obtain 164.8 g of a mixture of the polythiols of the above Formulae 8a to 8c.

Comparative Example 4: Preparation of a Polythiol

The procedures of Example 2 were repeated, except that, in Step (2), the amount of thiourea was 139.2 g (1.83 moles, about 1.07 equivalents per 1 equivalent of the polyol). In addition, in Step (3), it washed with an aqueous solution of 36% hydrochloric acid without further acid washing. Water washing was repeated until the pH of the waste liquid became 6 to 7. But thiourea was detected in the waste liquid. Thereafter, the same concentration under a reduced pressure and filtration were carried out to obtain 130.8 g of the polythiol of the above Formula 9.

Test Methods

The polythiols prepared in the Examples and the Comparative Examples were tested in the following manner. The results are summarized in Table 1 below.

(1) Residual Thiourea

The polythiol samples were tested to determine the presence of residual thiourea according to the following conditions.

Column: ACQUITY UPLC™ BEH Amide, 2.1×150 mm, 1.7 μm

Flow rate: 0.2 ml/minute, injection volume: 5.0 μl (PLNO), sample concentration: 10 μg/ml Sample dilution: MeCN/MeOH (75:25), 0.2% HCOOH, column temperature: 25° C., Weak Needle Wash: MeCN/H$_2$O (95:5)

Detection wavelength: 245 nm UV, sampling rate: 20 points/sec, filter time constant: 0.2

Device: Waters ACQUITY UPLC with ACQUITY UPLC PDA Detector

Figure 2:
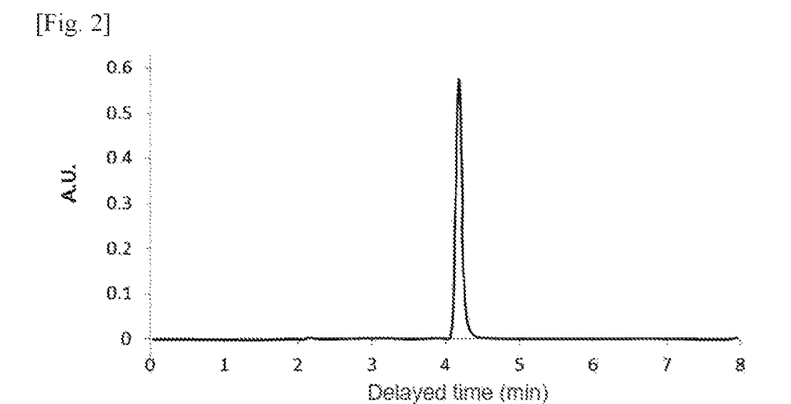
FIG. 2 is a result of the test for detecting residual thiourea in the polythiol sample prepared in Comparative Example 1.

Determined whether thiourea was present in the waste liquid for 4.2 minutes under the above conditions In addition, the test results of Comparative Example 1 are shown in FIG. 2, and the peak of residual thiourea could be confirmed.

(2) Hydroxyl Group

The polythiol samples were tested to determine the presence of hydroxyl groups at 3,400 to 3,500 cm$^{-1}$ through FT-IR analysis.

Figure 1:
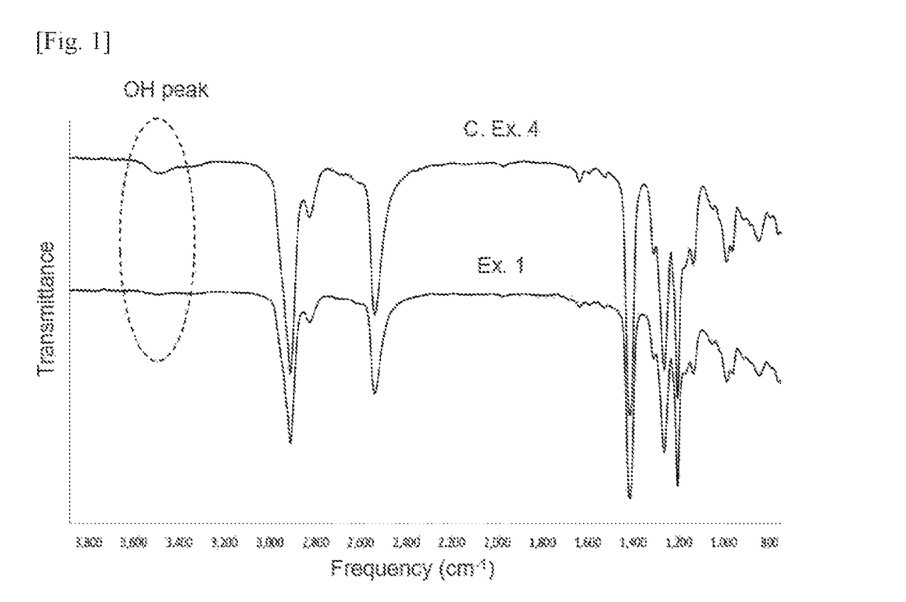
FIG. 1 is a result of FT-IR analysis for polythiol samples prepared in Example 1 and Comparative Example 4.

In addition, the results of FT-IR analysis for the polythiol samples of Example 1 and Comparative Example 4 are shown in FIG. 1. As can be seen from FIG. 1, a hydroxyl peak was observed in the curve of Comparative Example 4, which was not observed in the curve of Example 1.

(3) APHA Color

A standard solution was prepared in 5 units under APHA according to JIS K 0071-1 standard, and the color values of APHA (American Public Health Association) of the polythiol samples were observed with the naked eyes. In order to determine the correct color, the polythiol was filtered through a 0.2-μm PTEF filter to remove solid precipitates, and the color value was then measured.

(4) Thermal Discoloration

The polythiol samples were stored in an oven at 80° C. for 30 days, and the difference in APHA changed as compared with the initial value was measured.

(5) Precipitates

The polythiol samples were stored in an oven at 130° C. for 2 days, and the presence of precipitates was observed with the naked eyes.

(6) Storage Stability

In order to evaluate the storage stability of polythiol samples, the L* value in the CIE L*a*b* color coordinate was measured using a spectrophotometer (Colormate, Shinko Co., Ltd.) (D65 light source, 10°).

Here, a quartz cell having a width of 10 mm and washed clean with distilled water and acetone was used, and the baseline was calibrated by first measuring distilled water before each measurement.

The initial L* value (L*$_{initial}$) was measured within 1 day after the preparation of each polythiol sample, and the final L* value (L*$_{final}$) was measured after a certain period of time at each test temperature. The difference value (ΔL*) was then calculated.

TABLE 1

|  |  |  | Ex. 1 | Ex. 2 | Ex. 3 | Ex. 4 | Ex. 5 | C. Ex. 1 | C. Ex. 2 | C. Ex. 3 | C. Ex. 4 |
|---|---|---|---|---|---|---|---|---|---|---|---|
| Residual thiourea |  |  | x | x | x | x | x | o | o | x | o |
| Hydroxyl group |  |  | x | x | x | x | x | x | x | o | o |
| APHA color |  |  | 10 | 10 | 15 | 15 | 10 | 25 | 35 | 15 | 15 |
| Thermal discoloration |  |  | 10 | 5 | 10 | 10 | 5 | 15 | 20 | 15 | 15 |
| Precipitates (130° C., 48 hours) |  |  | x | x | x | x | x | o | o | x | x |
| Storage stability | $L^*_{initial}$ |  | 100.9 | 101.3 | 100.4 | 100.6 | 100.3 | 99.9 | 99.8 | 100.1 | 99.9 |
|  | 130° C., 8 hours | $L^*_{final}$ | 97.1 | 98.2 | 96.7 | 97.2 | 95.4 | 88.3 | 61.4 | 98.3 | 73.1 |
|  |  | $\Delta L^*$ | 3.8 | 3.1 | 3.7 | 3.4 | 4.9 | 11.6 | 38.4 | 1.8 | 26.8 |
|  | 60° C., 7 days | $L^*_{final}$ | 99.1 | 99.3 | 98.7 | 99.1 | 97.6 | 90.1 | 74.9 | 99.1 | 80.1 |
|  |  | $\Delta L^*$ | 1.8 | 2.0 | 1.7 | 1.5 | 2.7 | 9.8 | 24.9 | 1.0 | 19.8 |
|  | 15° C., 1 year | $L^*_{final}$ | 99.0 | 98.8 | 98.7 | 99.2 | 98.1 | 91.3 | 78.4 | 98.9 | 83.4 |
|  |  | $\Delta L^*$ | 1.9 | 2.5 | 1.7 | 1.4 | 2.2 | 8.6 | 21.4 | 1.2 | 16.5 |

As shown in Table 1, in the polythiols prepared in Examples 1 to 5, residual thiourea and hydroxyl groups were not observed, the color value of APHA was low, little discoloration was observed when they were stored under the conditions of high temperatures, and precipitates or cloudiness did not take place.

In contrast, it was difficult to remove residual thiourea even by acid washing and water washing from the polythiols of the Comparative Examples in which an excess of thiourea greater than the range of the Examples was used. In addition, in the polythiols of the Comparative Examples in which thiourea was used in an amount less than the range of the Examples, hydroxyl groups were observed, whereby the yield was lowered. In particular, when thiourea remained, the L* value was significantly lowered due to cloudiness in the evaluation of storage stability. In addition, the polythiols of the Comparative Examples had a large color value of APHA, the discoloration was significant when they were stored under the conditions of high temperatures, and precipitates or cloudiness took place.

The invention claimed is:

1. A process for preparing a polythiol, which comprises:
   reacting 1 equivalent of a polyol containing a sulfur atom with 1.11 to 1.30 equivalents of thiourea;
   hydrolyzing the reaction product to obtain a crude polythiol; and
   subjecting the crude polythiol to acid washing and water washing to remove unreacted thiourea in a waste liquid,
   wherein the acid washing is carried out twice or more,
   wherein the water washing is repeatedly carried out until the waste liquid has a pH of 6 to 7,
   wherein the polyol is a compound of the following Formula 6 or a compound of the following Formula 7:

[Formula 6]

[Formula 7]

and wherein the polythiol contains no residual thiourea.

2. The process for preparing a polythiol of claim 1, wherein the polyol is a compound of the following Formula 7, and the polythiol is a compound of the following Formula 8a:

[Formula 7]

[Formula 8a]

3. The process for preparing a polythiol of claim 1, wherein the polyol is a compound of the following Formula 7, and the polythiol is a mixture of compounds of the following Formula 8a to 8c:

[Formula 7]

[Formula 8a]

[Formula 8b]

[Formula 8c]

4. The process for preparing a polythiol of claim 1, wherein the polyol is a compound of the following Formula 6, and the polythiol is a compound of the following Formula 9:

5. The process for preparing a polythiol of claim 1, wherein the acid washing and water washing is repeatedly carried out until no thiourea is detected in the waste liquid.

6. The process for preparing a polythiol of claim 1, wherein the acid washing is carried out using an aqueous acid solution containing 1% by weight to 40% by weight of an inorganic acid selected from the group consisting of hydrochloric acid, nitric acid, sulfuric acid, phosphoric acid, boric acid, carbonic acid, hydrofluoric acid, and bromic acid.

\* \* \* \* \*